United States Patent
Garab et al.

(10) Patent No.: US 8,451,446 B2
(45) Date of Patent: May 28, 2013

(54) DIFFERENTIAL POLARIZATION MEASURING EXTENSION UNIT FOR A LASER-SCANNING MICROSCOPE

(75) Inventors: Gyözö Garab, Szeged (HU); Istvá Pomozi, Budapest (HU)

(73) Assignee: Magyar Tudomanyos Akademia Szegedi Biologiai Koezpont, Szeged (HU)

( * ) Notice: Subject to any disclaimer, the term of this patent is extended or adjusted under 35 U.S.C. 154(b) by 397 days.

(21) Appl. No.: 12/679,888

(22) PCT Filed: Sep. 26, 2008

(86) PCT No.: PCT/HU2008/000106
§ 371 (c)(1),
(2), (4) Date: Jun. 9, 2010

(87) PCT Pub. No.: WO2009/040591
PCT Pub. Date: Apr. 2, 2009

(65) Prior Publication Data
US 2010/0245822 A1    Sep. 30, 2010

(30) Foreign Application Priority Data

Sep. 28, 2007  (HU) ..................................... 0700635

(51) Int. Cl.
*G01J 4/00* (2006.01)
*G01J 3/30* (2006.01)
(52) U.S. Cl.
USPC .......................................... 356/365; 356/317
(58) Field of Classification Search
USPC .................. 356/365, 317, 445, 448
See application file for complete search history.

(56) References Cited

U.S. PATENT DOCUMENTS 5,748,318 A * 5/1998 Maris et al. .................... 356/630
6,856,391 B2 * 2/2005 Garab et al. ................... 356/366
(Continued)

FOREIGN PATENT DOCUMENTS
WO    WO-2008/081374 A2    7/2008

OTHER PUBLICATIONS

Hind Instruments, Photo elastic modulator, Dual PEM, http://www.hindsinstruments.com/products/photoelastic-modulators/dual-pem-systems/.*

(Continued)

*Primary Examiner* — Tarifur Chowdhury
*Assistant Examiner* — Sunghee Y Gray
(74) *Attorney, Agent, or Firm* — Birch, Stewart, Kolasch & Birch, LLP

(57) ABSTRACT

The invention relates to a differential polarizing laser-scanning microscope (DP LSM) for determining differential polarization quantities of a material, comprising a laser light source (L) for scanning the sample and illuminating it with a coherent and monochromatic light, a microscope unit (ME) with a sample holder for providing a preselected optical magnification and imaging and a polarization state setting unit (PAA) positioned in the illuminating beam path (between the light source and the sample holder). The microscope is further provided with detectors (D1, D2) in the observing beam path, at least one filter holder in front of the detectors and a signal-processing unit (VE) for processing the electrical signals of the detectors. In the DP-LSM microscope an optical element (DP) is located in the common beam path comprising the illuminating and the observing beams, for separating the orthogonal polarization components.

12 Claims, 3 Drawing Sheets

U.S. PATENT DOCUMENTS

Figure 1:
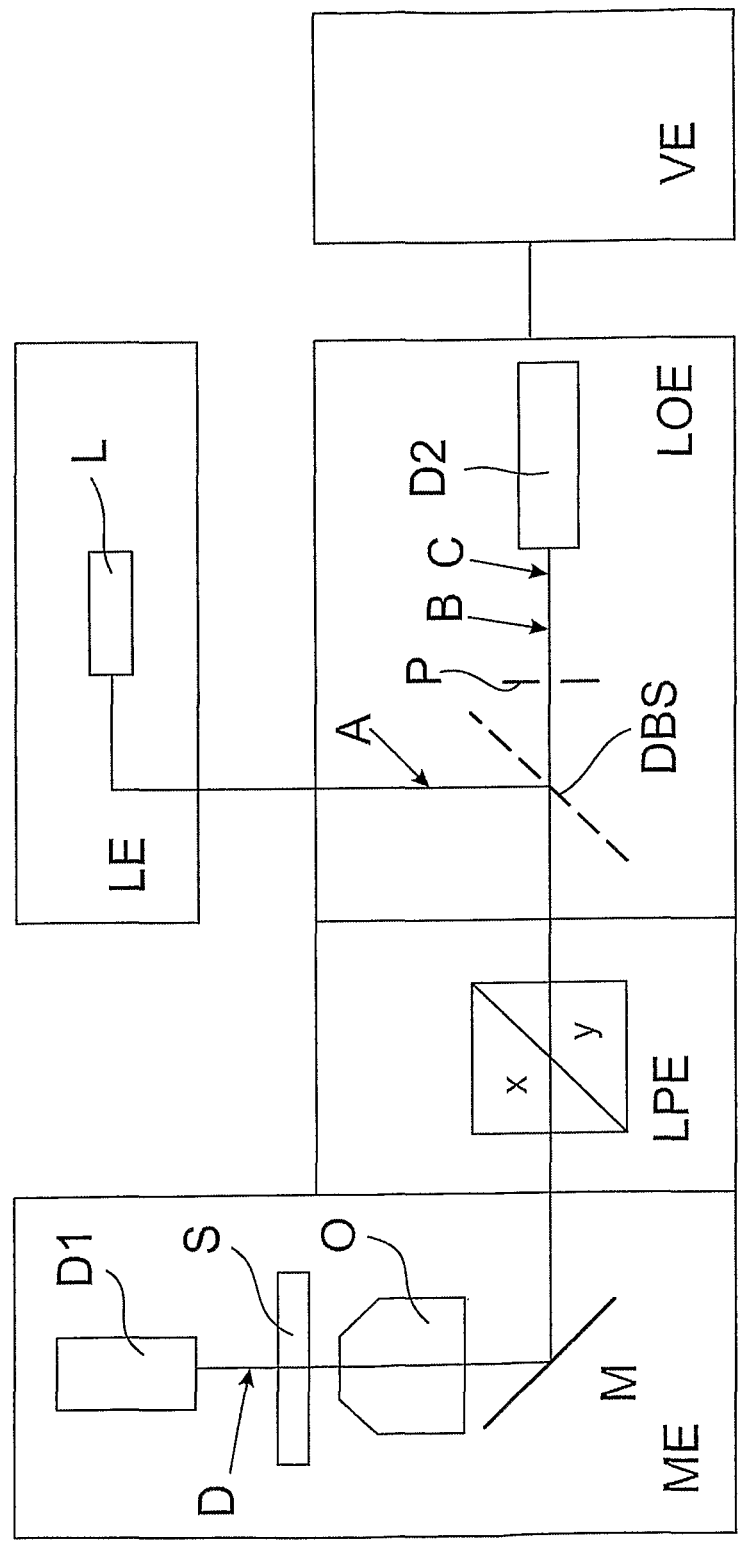

2003/0058442 A1  3/2003  Garab et al.
2004/0233434 A1* 11/2004 Wang .......................... 356/365

OTHER PUBLICATIONS

Horiba scientific, spectroscopic ellipsometry, http://www.horiba.com/scientific/products/ellipsometers/ellipsometry-tutorial/phase-modulation-spectroscopic-ellipsometer/what-are-the-advantages-of-the-photoelastic-modulator-over-others-forms-of-polarization-modulation/.*

Introduction lines 1-10 by Baoliang Wang, Optical Engineering, vol. 41, No. 5, pp. 981-987, May 2002, hereinafter Wang 2002'.*

Koopmans, B., et al. "In-plane optical anisotropy of GaAs/AlAs multiple quantum wells probed by microscopic reflectance difference spectroscopy", Applied Physics Letters, AIP, 1996, vol. 69, No. 6, pp. 782-784.

Santos, P.V., "Acoustic field mapping on GaAs using microscopic reflectance and reflectance anisotropy", Applied Physics Letter, AIP, 1999, vol. 74, No. 26, pp. 4002-4004.

Finzi, L. et al. "Design and application of a computer-controlled confocal scanning differential polarization microscope", Review of Scientific Instruments, AIP, 1998, vol. 59, No. 11, pp. 2399-2408.

* cited by examiner

DIFFERENTIAL POLARIZATION MEASURING EXTENSION UNIT FOR A LASER-SCANNING MICROSCOPE

Using a laser-scanning microscope (LSM) selected points (well defined volume units) of the tested material are irradiated by a focused laser beam in response of which information on the intensity of the transmitted, reflected or emitted light is obtained, which can be stored generally in digital form. The signal of the laser-scanning microscope during scanning a field of predetermined width and length is used to obtain a high-resolution picture for detailed analysis. The image quality may be further improved by using the LSM in confocal mode, thereby substantially excluding the disturbing effect of the light received from points other than the focal plane. In most of the commercially available laser-scanning microscopes (such as in Zeiss 410 or 510) the confocal mode is a basic feature, but it may be used only for the reflected or emitted light (fluorescence). The confocal mode of the LSM provides for a non-destructive optical slicing of the sample and a reconstruction of three-dimensional "images". Highly improved picture quality may be achieved by using a two or more photon laser excitation method which may be strictly limited to the tested area and thereby the disturbing effect of the background radiation (intensity) may be practically completely eliminated (A. Diaspro and M. Robello: Multi-Photon Excitation Microscopy to Study Biosystems, European Microscopy and Analysis, March 1999). Laser-scanning microscopes—when compared to the conventional microscopes and methods—provide a high quality and high-resolution information of the sample structure. Nevertheless, these methods do not provide any information on the anisotropy and many other physical interactions of the sample that may only be examined with polarization spectroscopy methods.

The use of polarized light provides images of the sample comprising information on the anisotropic structure, e.g. the spatial arrangement of the transition dipoles, and the physical interaction between each other and the microenvironment. The anisotropic properties of the materials typically influence the polarization properties of the light emitted, reflected or transmitted by the materials in an anisotropic way, therefore the examination of the polarization properties of the light emitted, reflected or transmitted by the materials enables conclusions relating to the optical anisotropy and also the molecular order of the tested material. Measurements carried out, with polarized light (LD: linear dichroism, CD: circular dichroism) are described by T. C. Oakberg in Application note, Stokes Polarimetry, Hinds Instruments Inc., 1991 news. A similar method can be used for measuring birefringence as well. The linear polarization of fluorescence emission provides important information on the anisotropy of the emission dipoles, therefore the anisotropy value (r) characteristic for this provides important information on the material structure not obtained by other techniques. The circular polarized luminescence (CPL) content of the emission (emitted light) provides information on the chiral structure in connection with the excited state of a substance, which may not be obtained in any other way. Further important information is the degree of polarization (P) of the fluorescence, which allows conclusion on energy transfer between the dipoles, the micro viscosity of the surroundings of the molecule, the lifetime of an excitation and other relevant parameters. The definition, measurement and physical content of P, r and CPL is specified in detail by J. R. Lakovicz in his book "Principles of Fluorescence Spectroscopy" and I. Z. Steinberg in his report published in Methods in Enzymology.

During differential polarization imaging as described in detail by Kim et al. in a report published in Biophysical Journal, two different images are produced of the sample using orthogonally polarized light, the intensity normalized difference of which provides information on the anisotropic structure of the material or sample. The values CD, LD and other differential polarization values of transmitted light defined by the Mueller matrix formulae carry information on the anisotropic structure of the material that cannot be obtained otherwise.

The polarization properties of the fluorescence (emitted light) may be determined by placing a polarizing component (e.g. a polarizing filter) in front of the detector of the LSM, rotating the polarizing filter between two angular positions for trajection of the orthogonal components of linear polarized light and taking two pictures subsequently in both positions of the polarizer filter, in principle. Although this method may be carried out with the accessories of the Zeiss LSM 410, it does not provide satisfactory results because of the variation of the intensity of fluorescence in time—especially in biological samples. A further problem may be the variation of the intensity of the illuminating laser light. Vibrations and movements of the sample or the stage may also lead to considerable distortions.

U.S. Pat. No. 5,457,536 suggests an improvement to Zeiss LSM, which makes the general purpose laser-scanning microscope capable of point-by-point measuring the dichroism and the birefringence of the light transmitted through the sample. During measurement, a polarization state generator interposed between the light source and the sample modulates the polarization state of the laser beam directed to the sample. The measurement is carried out on the beam transmitted through the sample with a polarization state-analyzing unit located on the side of object table opposite to the laser light source. The output of the analyzer is connected to a photodetector, which is connected with an output to a demodulating unit. One drawback of this configuration is that in most of the LSM-s the confocal mode is not available during LD, CD and birefringence measurements, which can only be carried out in transmission mode. This method does not enable the measurement of the polarization content of the emitted or reflected light; therefore it does not allow determining the anisotropy in the linear or circular polarization (r, CPL) of the emission (emitted light) and the grade of polarization (p) of the emission. This is a major drawback in studying biological samples where the confocal fluorescence microscopy is widely used. In most of the biological applications important information on the spatial arrangement of the different components can be obtained by following the emission of several chromophores. Each item of this information carries different polarization information, which cannot be analyzed with said conventional techniques. In many LSM-s it is not possible or it is very difficult to modulate the laser light because of the optical fiber coupling of the laser light. It is also disadvantageous that there is no possibility to characterize in full detail the polarization content of the light and therefore some of the important parameters of the light material intereaction—assigned to the Mueller matrix elements—cannot be determined. In an earlier publication (WO/2002/040953) of the applicant describes a method and apparatus for combining the advantages of laser-scanning microscopy (LSM) and polarimetry with the combination resulting in more measured parameters with a single apparatus, or with different configurations of a single apparatus with special regard to the differential polarization properties of emitted fluorescence measured in confocal mode at a single or multiple wavelengths at substantially the same time, or with regard to the possibly most complete analysis of the polarization content of emitted, transmitted or reflected light. In this method and apparatus a polarization state changing and/or modulating unit is positioned in each of the illuminating and/or measuring beam path, which may be controlled individually or together in order to determine the individual DP parameters for each position of the rastered light beam. It is however disadvantageous in this solution, that the main elements of the LSM have to be disconnected in order to allocate the units necessary for the measurement.

Most of the commercially available LSM-s (such as Zeiss 410 or 510) consist of a conventional microscope, a laser optical unit, a laser light source and the LSM control unit. Such LSM structures are known from DE 107 02 753, U.S. Pat. No. 6,167,173 and U.S. Pat. No. 6,947,127.

A conventional microscope can also be used without a laser light source and comprises an object table, an objective lens and an ocular. The laser optical unit typically forms a physically separated independent unit, which comprises an optical element for coupling the laser light, a beam expander, a main dichroic mirror for separating the illuminating laser light beam and the emitted fluorescent light beam and other optical elements: mirrors, beam splitters, filters, pinholes for eliminating the light received from outside the focal plane and detectors. The unit affecting the rastering of the laser light (LPE) is positioned between the conventional microscope unit and the laser optical unit, generally mounted integrally with the one or with the other unit. The configuration of the units is illustrated in FIG. 1. In a DP-LSM according to WO/2002/040953 the LSM shown in FIG. 1 is modified in order for the modulator to be located in Position A (CD, LD, FDLD, FDCD, LB, CB measurement), or in Position B (P, r measurement) and the analyzer in Position C (P, R measurement) or in Position D (LB, CB measurement). As it can be clearly seen, the conventional LSM in this prior art solution has to be disassembled at different locations, such as at the microscope and the laser optical unit. This involves the reconstruction of the whole apparatus resulting in higher complexity and higher costs of manufacturing.

It is an objective of the method and apparatus of the invention to provide a DP-LSM according to WO/2002/040953 in which the DP unit can be integrated into the LSM without the need for disassembling the laser optical unit or the conventional microscope unit of the LSM.

In order to achieve this objective an apparatus is provided, comprising:
- a laser light source for scanning the sample and illuminating it with a coherent and monochromatic light,
- a microscope unit with a sample holder for providing a preselected optical magnification and imaging,
- the possibility of placing a polarization state setting unit into the illuminating beam path (between the light source and the sample holder), wherein
- detectors in the observing beam path and an analyzer in front of the detectors, and
- a signal-processing unit for processing the electric signals of the detectors.

The differential polarizing laser-scanning microscope (DP-LSM) for determining the differential polarization quantities of substances according to the invention comprises:
- an optical element, located in the common beam path comprising the illuminating and the observing beams, for separating the orthogonal polarization components in time.

In a preferred embodiment the optical element for separating the orthogonal polarization components in time is located between the microscope unit and the unit for deflecting the laser beam.

Such a configuration can be used in providing DP-LSM systems in which there is no need for disassembling the main units of a conventional LSM system, as the new elements can be accommodated in a space between the main units of the conventional LSM system. Therefore, the DP-LSM system according to the invention provides a solution that can be used in addition to conventional LSM systems, and is easy to manufacture as an extension unit or adapter to be integrated into any existing LSM system. The existing conventional LSM systems need not to be disassembled or modified at all.

Figure 2:
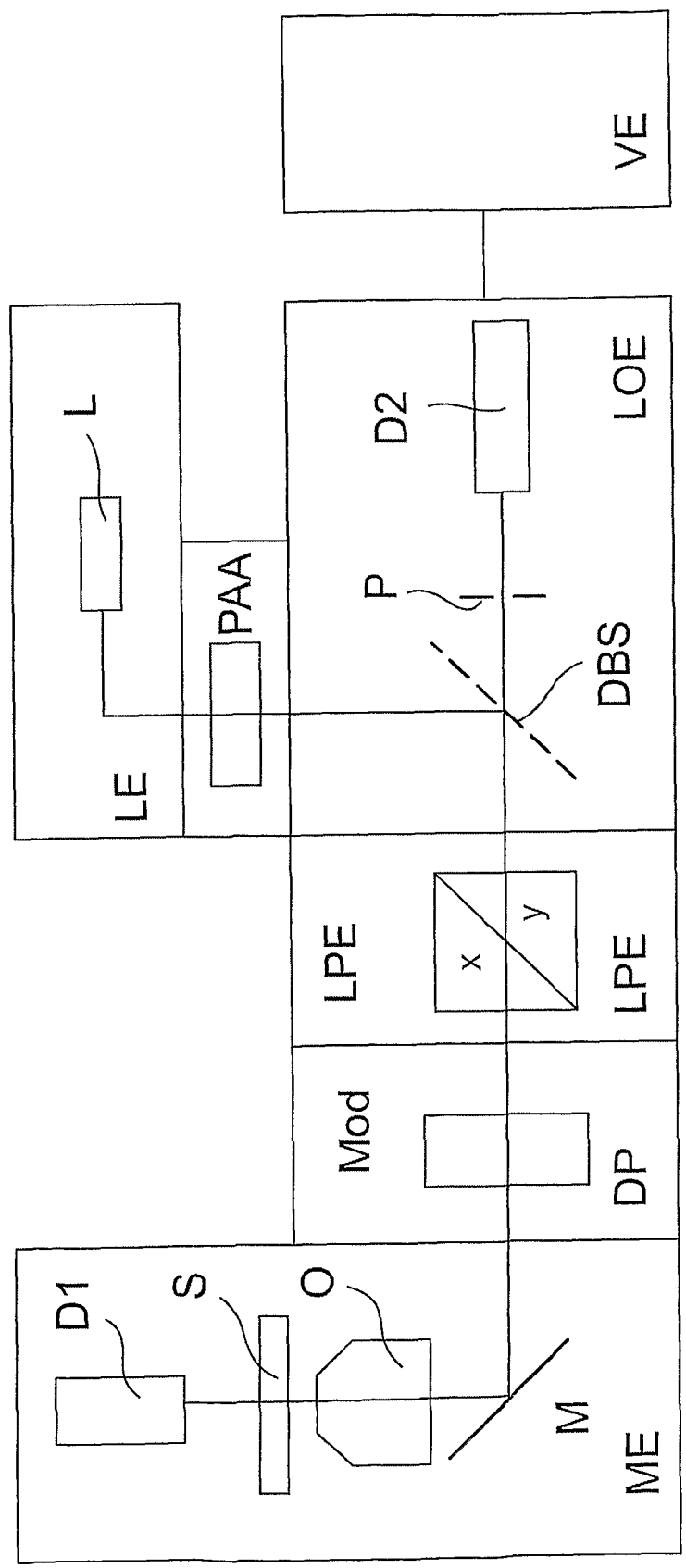
Figure 3:
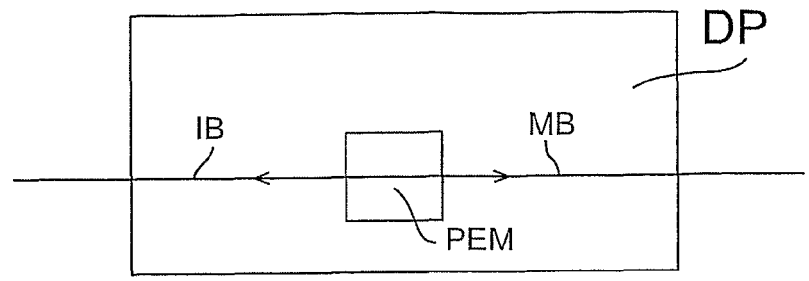
Figure 4:
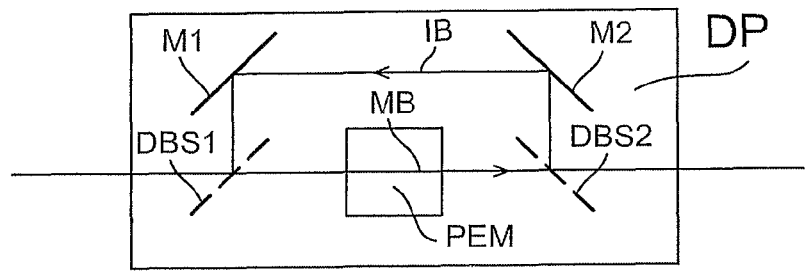
Figure 5:
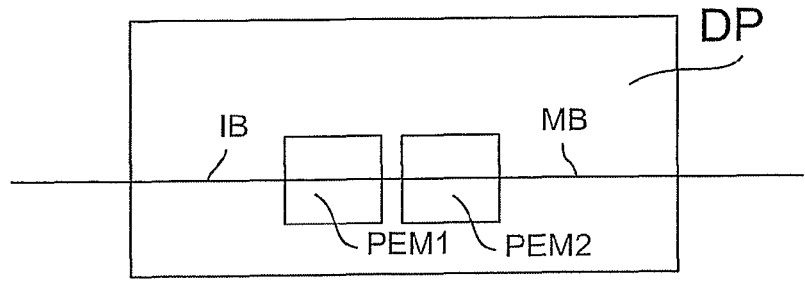
Figure 6:
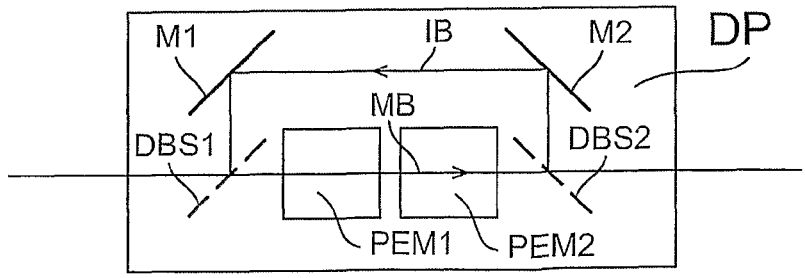

The invention will be described in more detail according to the accompanying drawings, wherein FIG. 1 is a schematic block diagram of a conventional LSM system with the prior art DP-LSM extension units, FIG. 2 a structural block diagram of a DP-LSM system according to the invention, FIG. 3 is a first embodiment of a modulator unit that can be used in the system of FIG. 2, FIG. 4 is a second embodiment of a modulator unit that can be used in the system of FIG. 2, FIG. 5 is a third embodiment of a modulator unit that can be used in the system of FIG. 2, and FIG. 6 is a fourth embodiment of a modulator unit that can be used in the system of FIG. 2.

FIG. 1 illustrates the block diagram of a conventional laser-scanning microscope (LSM) with the main structural units. An LSM such as disclosed in DE 107 02 753 comprises a microscope unit ME, a laser optical unit LOE connected to the microscope unit and a laser unit LE and a control unit VE both connected to the laser optical unit. Laser unit LE comprises a laser light source L, the laser light of which is incident on a main dichroic mirror DBS located in the laser optical unit LOE that is connected to the laser unit LE, for separating the illuminating beam and observing beam also comprising the fluorescent emission. Also comprised in the laser optical unit is a pinhole P for eliminating the light received from outside the focal plane and at least one detector D2. The laser beam scanning unit LPE connected to (or integrated with) the laser optical unit provides for the rastering of the laser beam generated by laser light source L and deflected by the dichroic beam splitter DBS. The rastering means a deflecting in two substantially perpendicular directions with one direction being defined by scanning the pixels of a line (preferably in pixel by pixel increments) and the other direction being defined by scanning the lines of an image (preferably in line by line increments). The term "image", within the context of the invention, is used to designate the image of the sample on the object table. The laser-scanning unit LPE is shown in FIG. 1 external to the laser optical unit LOE, but it is also possible to accommodate the laser-scanning unit LPE within the laser optical unit LOE as an integral part thereof. Beside this, the scanning of the sample by the laser light may be accomplished by rastering the scanning stage as well. Filter holders may also be provided in front of the detectors for receiving color filters or polarizing filters.

The illuminating laser beam passes from the laser-scanning unit LPE into the microscope unit ME, which accommodates a mirror M, an objective O, a sample holder S and a detector D1. The microscope unit generally also comprises an ocular through which the sample may be observed. The microscope unit alone, without the other units may be used as a conventional microscope.

In a DP-LSM according to WO/2002/040953 the LSM shown in FIG. 1 is modified in order for the modulator (e.g. a photo-elastic modulator) to be located in Position A (CD, LD, FDLD, FDCD, LB, CB measurement), or in Position B (P, r and CPL measurement) and the analyzer in Position C (P, R measurement) or in Position D (LB, CB measurement). As it can be clearly seen in the drawing, in the prior art DP-LSM system one of the modulator or analyzer is located in the illuminating beam path and the other in the observing beam path. For proper functioning, a basic feature is to control the modulator and the analyzer in a synchronized manner to maintain phase adjustment.

In FIG. 2 a DP-LSM system according to the present invention is shown, in which the polarization state setting unit PAA is located between the laser unit LE and the laser optical unit LOE, and the differential polarizing unit DP is positioned between the microscope unit ME, and the laser-scanning unit LPE. As shown in the drawing, the differential polarizing unit DP is positioned in a common beam path comprising both the illuminating and the observing beam path. The DP unit comprises a modulator for effecting a modulation by modulating the phase of the polarization components orthogonal to each other (like in PEM of FIG. 3). A filter holder in front of the detector D1 or D2 may receive an analyzer, such as a polarizing filter. As the filter holder may be removed from the LSM, a filter change does not involve a disassembling of modifying of the system. With this configuration—as described below in more detail, and with the optical element adjusted accordingly—it will be possible to measure anisotropy (r), circular polarization (CPL) of luminescence, linear and circular dichroism (FDLD, FDCD) of fluorescence, the linear and circular dichroism (LD, CD) and birefringence (LB and CB). For the conventional measuring of the grade of polarization (P) (at constant polarization of the exciting light, using alternating analyzer for determining the intensity of the components parallel and orthogonal to the exciting polarization), a modified DP unit will be described. A shown in the drawing, the DP unit is located between the microscope unit De and the laser-scanning unit LPE, but identical effect may be achieved when the DP unit and the laser-scanning unit LPE are interchanged, for example when the laser-scanning unit LPE is integrated into the microscope unit ME.

The signal-processing, e.g. the demodulation of the detector signals and the calculation of the polarization values is accomplished as described in WO/2002/040953. The detector signal is fed to the signal-processing unit, which also controls the DP unit. The real time DP values are obtained at the output of the electronic signal-processing unit and/or they can be displayed on an external monitor (not part of the LSM). The output of the electronic signal-processing unit may also be fed to the LSM and thus the DP images may be displayed or processed in the LSM system as well. The feedback may be accomplished in two ways:

Analog: providing a detector type signal as generated by a detector, the central unit of LSM does not realize any difference, disassembling not necessary.

Digital: the detector signals will be coupled to the central unit of the LSM after digitizing.

A main advantage of the method is, that the method of WO/2002/040953 may be performed slightly modified but without any decrease in the accuracy, and the DP extension is easier and therefore more economical to combine with the LSM systems.

The modulator in this method will be placed between the conventional microscope and the laser optical unit, more specifically between the main dichroic beam splitter and the sample in the common light beam path, where the illuminating laser light and the light emitted or reflected by the sample are present simultaneously, but with an opposite direction of propagation. The main dichroic beam splitter is used for separating the illuminating laser light from the fluorescent light in order to provide the detectors only with the light emitted by the sample. In case of reflected light a semitransparent mirror may be used as well, instead of the dichroic beam splitter. Making use of this common beam path, the modulator placed here is capable of modulating the polarization of any of the illuminating or reflected/emitted light, depending of the type of measurement. Of course, the modulation will affect also the polarization of the other light beam not to be modulated, but it will not cause any problem as discussed in more detail below.

Measuring of Anisotropy and Circular Polarization of Luminescence (r, CPL)

When measuring the linear or circular anisotropy r or CPL of fluorescence (or reflected light), the sample is excited with a depolarized laser light (using the polarization state setting unit PAA); the magnitude of anisotropy may be determined as a ratio of the intensity difference of polar components of the polarized fluorescence according to the grade of anisotropy of the sample, and the average intensity. The polarization state setting unit PAA depolarizes the illuminating light, which then passes through the optical unit DP and stays depolarized (in the depolarized light each phase between the two orthogonal polarization components are present, thus the depolarized state is not affected by a delay of the components). The emitted/reflected light (which propagates in opposite direction to the illumination) will be modulated at the wavelength of the measurement. With the analyzer (which may be a passive optical element for linear polarization) in front of the detector (in position C) the phase modulation is converted to intensity modulation, which will serve for measuring the intensity of the two distinguished fluorescent or reflected light components polarized orthogonally. When using a photo-elastic modulator PEM as a modulator for measuring anisotropy r, the modulation amplitude is $\lambda/2$, the demodulation frequency is 2f, or the modulation amplitude is $\lambda/4$ and the optical unit DP also comprises a $\lambda/4$ phase retarder (for providing a maximum phase delay of $\lambda/4$), the demodulation frequency may be f, with A being the wavelength of the observed reflected/emitted light. For CPL measurements the amplitude of PEM is $\lambda/4$, the analyzer is a linearly polarizing passive optical element, and the PEM demodulation frequency may be f.

Linear and Circular Dichroism (LD, CD)

The system remains suitable for measuring dichroism, because the modulator is located between the laser light source with a polarization state adjusted by PAA and the sample, and the light transmitting through the sample (not passing through the modulator again) is detected.

When measuring LD and CD, the polarization state of the laser beam will be periodically changed. Because of the differential absorption of the sample or, in more general terms, because of the differential extinction of light, the intensity of two different (typically orthogonally) polarized light components with the same intensity will change when passing through the sample, which may be measured with detector D1. The magnitude of LD and CD may be determined from the difference of the two beam intensities, when knowing the intensity of incident light or the average of the intensities of light of the two polarization states. The basic polarization state of the laser may be set by the polarization state setting unit PAA. The polarization of illuminating laser light is modulated (in order to provide different orthogonal polarization states subsequently) in the optical unit DP by a phase modulator (such as photo-elastic modulator PEM). The measurement is carried out on the light passing through the sample, therefore the measuring beam does not pass the modulator again and no analyzer will be needed. When measuring LD, the polarization state setting unit PAA provides linear polarization, the PEM amplitude is $\lambda/2$, the demodulation frequency is 2f, or PAA provides circular polarization, the PEM amplitude is $\lambda/4$, the PEM demodulation frequency is f. Alternatively, the PAA provides linear polarization, the DP unit also comprises a $\lambda/4$ phase retarder, the PEM amplitude is $\lambda/4$, the PEM demodulation frequency may be f.

For performing CD measurements, the polarization state setting unit PAA provides linear polarization, the PEM amplitude is $\lambda/4$ and the PEM demodulation frequency is f.

Fluorescence Detected Linear and Circular Dichroism (FDLD, FDCD)

In measuring FDLD or FDCD of fluorescent chromophores when the intensity of fluorescence is proportional to the intensity of absorbed light, the difference of the fluorescence intensities of the two polarization states are proportional to the value of LD and CD. These values can be measured in the same way as LD and CD, with the difference, that the intensity of emitted light is measured with detector D2. The reflected/emitted light crosses again the phase modulator in a direction opposite to the illuminating light; this however does not change the intensity of light (only the polarization state, analyzer not needed). In FDLD and FDCD measurements the polarization of the emitted light is not measured, therefore the result of measurement is not influenced. (The polarization of illuminating light is modulated and the intensity of the emitted light is demodulated; this intensity is not influenced by the crossing of the modulator.)

The measurements can also be accomplished by using the detector D1. To this end, a color filter may be used for separating the fluorescence light and the laser light at position D.

Linear and Circular Birefringence (LB, CB)

The system remains suitable for measuring birefringence, because the modulafor is located between the laser light source with a polarization state adjusted by PAA and the sample and the light transmitted through the sample is detected with detector D1, also using the analyzer in position D. (The light does not cross again the modulator.) The measuring process is substantially identical with the method described in WO/2002/040953 and in an article by Garab et al. published in Eur Biophys J, 2005.

Grade of Polarization (P)

Measuring of P according to an arrangement of FIG. 2 may be performed by selecting a linear polarization with PAA, the modulator amplitude may be set in a similar way as described in connection with the measurement of FDLD, wherein an analyzer (e.g. a linear polarizing filter) and a color filter is used for separating the fluorescence (emitted) and the exciting (illuminating) light in position D. An arrangement for measuring the grade of polarization with detector D2 (which is generally suitable for confocal measuring) is shown in FIG. 4. The reflected/emitted light will be modulated while the polarization of the illuminating light should be maintained. The polarization of the illuminating light would be changed when passing through the modulator in an undesired way, therefore the modulator shall be circumvented by using two dichroic beam splitters DBS1, DBS2 and two mirrors M1, M2.

FIG. 4 illustrates a possible embodiment of the optical units that can be used for measuring the grade of polarization. The dichroic beam splitters DBS1, DBS2 reflect the illuminating laser light in order to by-pass the modulator, while transmitting the emitted light (with a longer wavelength) through the photo-elastic modulator PEM.

Using a photo-elastic modulator PEM as a modulator, the modulation amplitude is $\lambda/2$, the demodulation frequency is 2f, or the modulation amplitude is $\lambda/4$ and the optical unit DP also comprises a $\lambda/4$ phase retarder between the dichroic beam splitters, the demodulation frequency may be f, with A being the wavelength of the observed emitted light.

This arrangement can be used for a conventional measuring of the grade of polarization P: at constant polarization state of the exciting light, using alternating analyzer for determining the intensity of the components parallel and orthogonal to the exciting polarization.

Analysis of the Polarization Content of the Reflected Light

The measurements for determining fluorescent emission values r, CPL, FDLD and FDCD can also be used for determining the polarization content of the reflected light with detector D2. In this measurement a semitransparent mirror shall be used instead of the main dichroic mirror. The measuring process is in every other aspect identical to the method as described above. Therefore, these measurements are suitable for determining the reflection Mueller-matrix parameters pixel-by-pixel.

Structure of the PAA and DP Optical Units:

The polarization state setting unit PAA may have different forms as described in WO/2002/040953. It may be empty, thus not changing the polarization state of the laser light, or it may comprise a passive optical element for setting the polarization state of the laser light according to the measurement to be performed, e.g. an optical phase retarder plate, a polarizer or a depolarizer, or a combination thereof. As an example, a linear polarization may be achieved by a linear polarizer, and a circular polarization may be obtained by using a $\lambda/4$ phase retarder behind the polarizer.

The optical unit DP may comprise beside the modulator (or mirrors and beam splitters in an alternative form measuring the grade of polarization) passive optical elements, such as an optical phase compensator (phase retarder). The anisotropy, the grade of polarization, and the linear dichroism as well may be determined more exactly by inserting a $\lambda/4$ plate (detailed description above).

In the method describe in WO/2002/040953, the optical unit DP may also cornprise two modulators (see FIGS. 5 and 6), which operate at different frequencies and help to determine all of the polarization quantities: the linear birefringence, the anisotropy, the grade of polarization with direction and magnitude.

Determining the Stokes Parameters and the Mueller Matrix:

Using an optical unit DP modified for measuring the grade of polarization (FIGS. 4 and 6) the Stokes parameters (I, Q, U, V) of a fluorescence or reflection for a laser light of a given polarization may be determined according to the method described in WO/2002/040953.

The fluorescence response signal or all of the Mueller matrix elements of reflected light can be determined, if an illuminating light with a proper polarization state is provided by PAA, and a properly configured optical unit DP is used.

Corrections:

The polarization distortions of the system may be compensated with different procedures. The Mueller matrix elements corresponding to the distortions may be determined and the distortions may then be compensated by a computer program, or the necessary phase corrections may be performed with a phase compensator within the DP unit. The linear polarization state of the exciting (illuminating) light may be influenced by certain optical components of the microscope, resulting in a change of the LD and FDLD values, that can be compensated by a computer program. In other cases, the circularly polarized state of the exciting light may be converted by the optical elements of the microscope to be elliptically polarized resulting in an undesired phase shift, which may be compensated by a phase compensator. The two methods can also be combined, if necessary.

Summary:

The optical path of the illuminating light:
instead of
laser source->modulator->main dichroic beam splitter->sample
laser source->main dichroic beam splitter->modulator->sample The optical path of the reflected/emitted light:
instead of
sample->main dichroic beam splitter->modulator->detector
sample->modulator->main dichroic beam splitter->detector Positioning the modulator in the common beam path between the main dichroic beam splitter and the sample, an improved DP-LSM system is obtained that does not require to brake the integrity of the LSM system. The modified optical arrangement enables also the measuring of the differential polarization (DP) quantities as described above in more detail.

In order to perform DP measurements an existing LSM has to be completed by a DP optical unit, which can be easily inserted between the conventional microscope and the laser optical unit; a PAA, which can be easily inserted between the laser source and the laser optical unit; an analyzer that can be inserted in a filter holder in front of the detector and a DP control unit.

As long as the modulator is switched off, the LSM may be operated in a conventional mode. A further advantage of the invention is that the measurements can be effected with less moving parts, and a single modulator is sufficient for determining the described DP quantities, while in the method as described in WO/2002/040953, two modulators are needed (one between the laser source and the main dichroic mirror and one between the main dichroic mirror and the detector. Additional advantages and modifications will be apparent to those skilled in the art. Therefore, the invention in its broader aspects is not limited to the specific details and illustrated examples shown and described herein. Accordingly, various modifications may be made without departing from the spirit or scope of the general inventive concept as defined by the appended claims and their equivalents.

The invention claimed is:

1. A differential polarization laser-scanning microscope (DP-LSM) for determining differential polarization quantities of a material, comprising:
a laser light source (L) for scanning the sample and illuminating it with a coherent and monochromatic light,
a microscope unit (ME) with a sample holder for providing a preselected optical magnification and imaging,
a polarization state setting unit (PAA) positioned in the illuminating beam path (between the light source and the sample holder), wherein
detectors (D1, D2) in the observing beam path and at least one filter holder in front of the detectors, and
a signal-processing unit (VE) for processing the electric signals of the detectors, and
an optical element (DP), located in the common beam path comprising the illuminating and the observing beams, for separating the orthogonal polarization components, wherein optical elements for separating the illuminating and observing light beam are provided on both sides of the photo-elastic modulator (PEM) or electro-optical unit.

2. The microscope of claim 1, wherein the optical element (DP) for separating the orthogonal polarization components is located between the microscope unit (ME) and the laser optical unit (LOE).

3. The microscope of claim 2, wherein the optical element (DP) for separating the orthogonal polarization components is a photo-elastic modulator (PEM) or another electro-optical unit, for periodically or programmable changing the polarization state of light.

4. The microscope of claim 3, wherein the separating elements on both sides of the photo-elastic modulator (PEM) or electro-optical unit are mirrors (M1, M2) and dichroic beam splitters (DBS1, DBS2).

5. The microscope of claim 4, wherein the separating units on both sides of the photo-elastic modulator (PEM) or electro-optical unit are dichroic beam splitters (DBS1, DBS2).

6. The microscope of claim 2, wherein the optical elements for separating the orthogonal polarization components are photo-elastic modulators (PEM1, PEM2) or electro-optical units.

7. A laser-scanning microscope (LSM) for determining differential polarization quantities of a sample, comprising:
a laser light source (L) for generating a coherent and monochromatic light,
a laser optical unit (LOE) with a dichroic beam splitter (DBS) and a laser scanning unit (LPE) for scanning the laser beam onto the sample and illuminating it with the laser light,
a polarization state setting unit (PAA) between the laser light source (L) and the laser optical unit (LOE),
a microscope unit (ME) with a sample holder (S), a mirror (M), and an objective (O) arranged on the optical axis between the sample holder (S) and the mirror (M), for providing a preselected optical magnification and imaging,
a detector (D1) attached to the microscope unit (ME) for detecting an observing beam transmitted through the sample and a detector (D2) attached to the laser optical unit (LOE) for detecting the reflected or fluorescent observing beam received from the sample, and
a signal-processing unit (VE) for processing the electric signals of the detectors (D1, D2), and
a DP extension unit, in the form of an optical element (DP), located between the microscope unit (ME) and the laser optical unit (LOE) in the common beam path comprising the illuminating laser beam and the observing reflected laser beam or fluorescence emission elicited by the laser beam, for separating the orthogonal polarization components either of the illuminating laser beam or of the observing beam, in time.

8. The microscope of claim 7, wherein the a DP extension unit for separating the orthogonal polarization components is a photo-elastic modulator (PEM) or another electro-optical unit, for periodically or programmably changing the polarization state of light.

9. The microscope of claim 8, wherein optical elements for separating the illuminating and observing light beam are provided on both sides of the photoelastic modulator (PEM) or electro-optical unit.

10. The microscope of claim 9, wherein the separating elements on both sides of the photo-elastic modulator (PEM) or electro-optical unit are mirrors (M1, M2) and dichroic beam splitters (DBS1, DBS2).

11. The microscope of claim 10, wherein the mirrors on both sides of the photo-elastic modulator (PEM) or electro-optical unit are dichroic beam splitters (DBS1, DBS2).

12. The microscope of claim 11, wherein the optical elements for separating the orthogonal polarization components are photo-elastic modulators (PEM1, PEM2) or electro-optical units.

* * * * *